(12) United States Patent
Murphy et al.

(10) Patent No.: US 10,127,654 B2
(45) Date of Patent: Nov. 13, 2018

(54) MEDICAL IMAGE PROCESSING APPARATUS AND METHOD

(71) Applicant: Toshiba Medical Systems Corporation, Otawara-shi (JP)

(72) Inventors: Sean Murphy, Edinburgh (GB); Keith Goatman, Edinburgh (GB); Ian Poole, Edinburgh (GB)

(73) Assignee: Toshiba Medical Systems Corporation, Otawara-shi (JP)

(*) Notice: Subject to any disclaimer, the term of this patent is extended or adjusted under 35 U.S.C. 154(b) by 43 days.

(21) Appl. No.: 14/876,906

(22) Filed: Oct. 7, 2015

(65) Prior Publication Data

US 2017/0103518 A1    Apr. 13, 2017

(51) Int. Cl.
*G06K 9/00* (2006.01)
*G06T 7/00* (2017.01)
(Continued)

(52) U.S. Cl.
CPC .......... *G06T 7/0012* (2013.01); *A61B 8/0858* (2013.01); *A61B 8/461* (2013.01); *A61B 8/467* (2013.01); *A61B 8/5215* (2013.01); *G06T 7/11* (2017.01); *G06T 7/136* (2017.01); *G06T 7/60* (2013.01); *G06T 2207/10132* (2013.01); *G06T 2207/30044* (2013.01); *G06T 2207/30096* (2013.01); *G06T 2207/30196* (2013.01)

(58) Field of Classification Search
CPC ....... A61B 8/0858; A61B 8/461; A61B 8/467; A61B 8/5215; G06T 2207/10132; G06T 2207/30044; G06T 2207/30196; G06T 7/0012; G06T 7/0081
See application file for complete search history.

(56) References Cited

U.S. PATENT DOCUMENTS

| 8,879,813 | B1* | 11/2014 | Solanki | G06T 7/0014 382/128 |
| 2002/0028008 | A1* | 3/2002 | Fan | G06T 7/0012 382/131 |

(Continued)

FOREIGN PATENT DOCUMENTS

| JP | 2006-234798 A | 9/2006 |
| JP | 2010-207596 A | 9/2010 |
| JP | 2013-39156 A | 2/2013 |

OTHER PUBLICATIONS

GE Healthcare, "Ultrasound Imaging: Assisted Reproductive Medicine", 2012, 2 pages.

(Continued)

*Primary Examiner* — Tom Y Lu

(74) *Attorney, Agent, or Firm* — Oblon, McClelland, Maier & Neustadt, L.L.P.

(57) ABSTRACT

A medical image processing apparatus comprises a memory configured to store medical image data representative of a tissue structure and a processing circuitry configured to operationally connect to the memory, extract regions from the medical image data by performing threshold processing of the medical image data using each of a plurality of threshold values, select regions meeting at least one predetermined condition from among the extracted regions, and determine a region representative of the tissue structure in the medical image data based on the selected regions.

20 Claims, 8 Drawing Sheets

(51) Int. Cl.
  *A61B 8/08* (2006.01)
  *A61B 8/00* (2006.01)
  *G06T 7/60* (2017.01)
  *G06T 7/11* (2017.01)
  *G06T 7/136* (2017.01)

(56) References Cited

U.S. PATENT DOCUMENTS

2004/0252870 A1* 12/2004 Reeves ................ G06T 7/0012
  382/128
2010/0310146 A1* 12/2010 Higgins ................ G06T 7/162
  382/131
2016/0314335 A1* 10/2016 Al-Kofahi ............ G06K 9/0014

OTHER PUBLICATIONS

Terrence Chen et al., "Automatic Ovarian Follicle Quantification from 3D Ultrasound Data Using Global/local Context with Database Guided Segmentation", Computer Vision, 2009, IEEE 12$^{th}$ International Conference on, 8 pages.
P. S. Hiremath et al., "Follicle Detection and Ovarian Classification in Digital Ultrasound Images of Ovaries", Advancements and Breakthroughs in Ultrasound Imaging, edited by Gunti Gunarathne, ISBN 978-953-51-1159-7, chapter 7, 33 pages.
P.S. Hiremath et al., "Speckle Noise Reduction in Medical Ultrasound Images", Advancements and Breakthroughs in Ultrasound Imaging, edited by Gunti Gunarathne, ISBN 978-953-51-1159-7, chapter 8, 41 page.

* cited by examiner

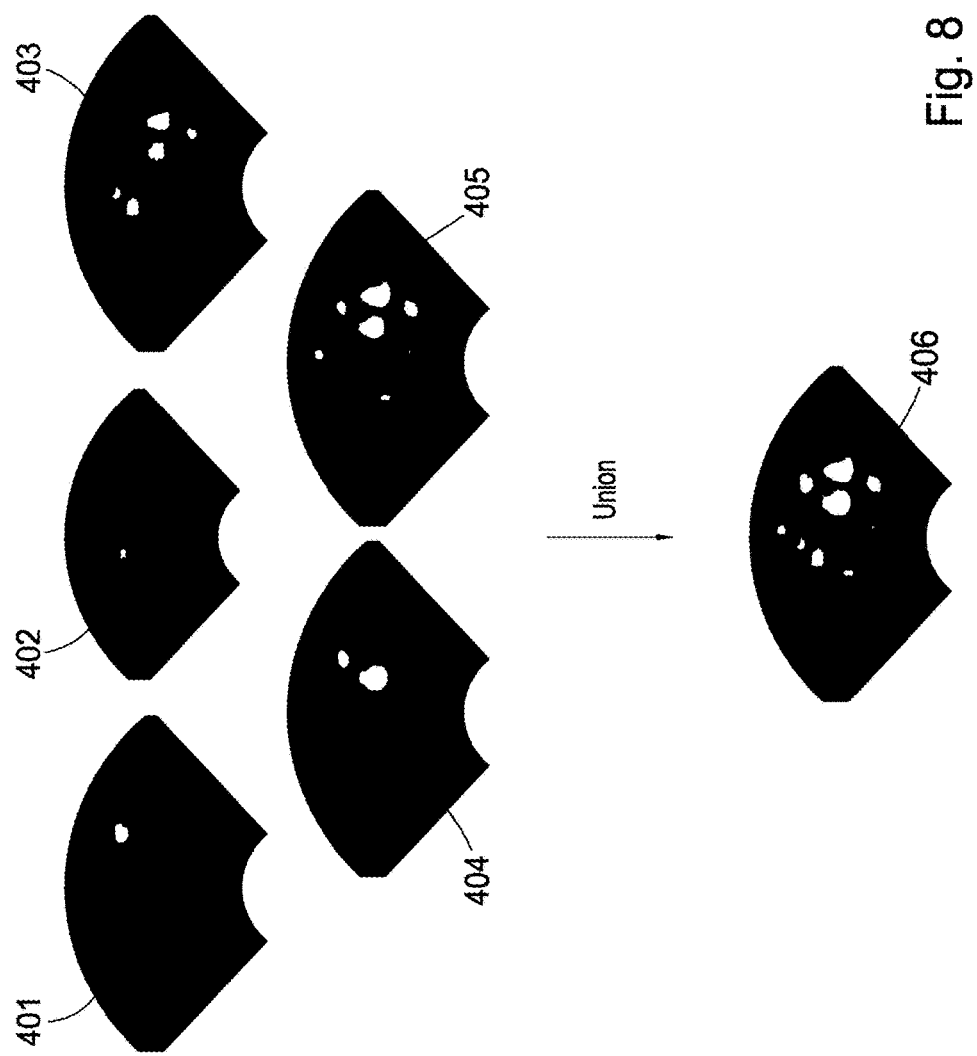

MEDICAL IMAGE PROCESSING APPARATUS AND METHOD

FIELD

Embodiments described herein relate generally to a method of, and apparatus for, processing medical imaging data, for example for segmenting medical imaging data. Certain embodiments relate, for example, to segmentation of ovarian follicles in ultrasound data.

BACKGROUND

The success of in-vitro fertilization (IVF) may rely on careful monitoring and stimulation of the ovulation process. A patient's ovaries may be regularly scanned with transvaginal ultrasound (also known as endovaginal or EV ultrasound) to monitor the growth of ovarian follicles. A steady increase in the number and/or diameter of the follicles may indicate that the patient is responding well to treatment. Once an adequate number of follicles are present and the follicles reach a predetermined size, eggs may be aspirated, fertilized and re-implanted (or may be frozen).

Manual counting and measurement of follicles may be tedious and/or may be prone to human error.

Segmentation may represent the process of identifying pixels or voxels representing a given structure in an image or set of image data, which may include separating the pixels or voxels from the rest of the image or set of image data.

Ultrasound images may be noisy, for example due to speckle. Ultrasound images may also be prone to artifacts, for example acoustic shadows. Reverberation artifacts may artificially raise the intensity of an object. Furthermore, the intensity level of an ultrasound image may be arbitrary and may vary across an image. The variation in intensity level of the ultrasound image can make segmentation in ultrasound particularly challenging.

BRIEF DESCRIPTION OF THE DRAWINGS

Embodiments are now described, by way of non-limiting example, and are illustrated in the following figures, in which:

FIG. 8 is representative of the union of selected regions obtained using several different threshold values.

DETAILED DESCRIPTION

Certain embodiments provide a medical image processing apparatus comprising a memory configured to store medical image data representative of a tissue structure and processing circuitry configured to operationally connect to the memory, extract regions from the medical image data by performing threshold processing of the medical image data using each of a plurality of threshold values, select regions meeting at least one predetermined condition from among the extracted regions, and determine a region representative of the tissue structure in the medical image data based on the selected regions.

Certain embodiments provide a medical image processing method comprising operationally connecting to a memory in which is stored medical image data representative of a tissue structure, extracting regions from the medical image data by performing threshold processing of the medical image data using each of a plurality of threshold values, selecting regions meeting at least one predetermined condition from among the extracted regions, and determining a region representative of the tissue structure in the medical image data based on the selected regions.

Figure 2:
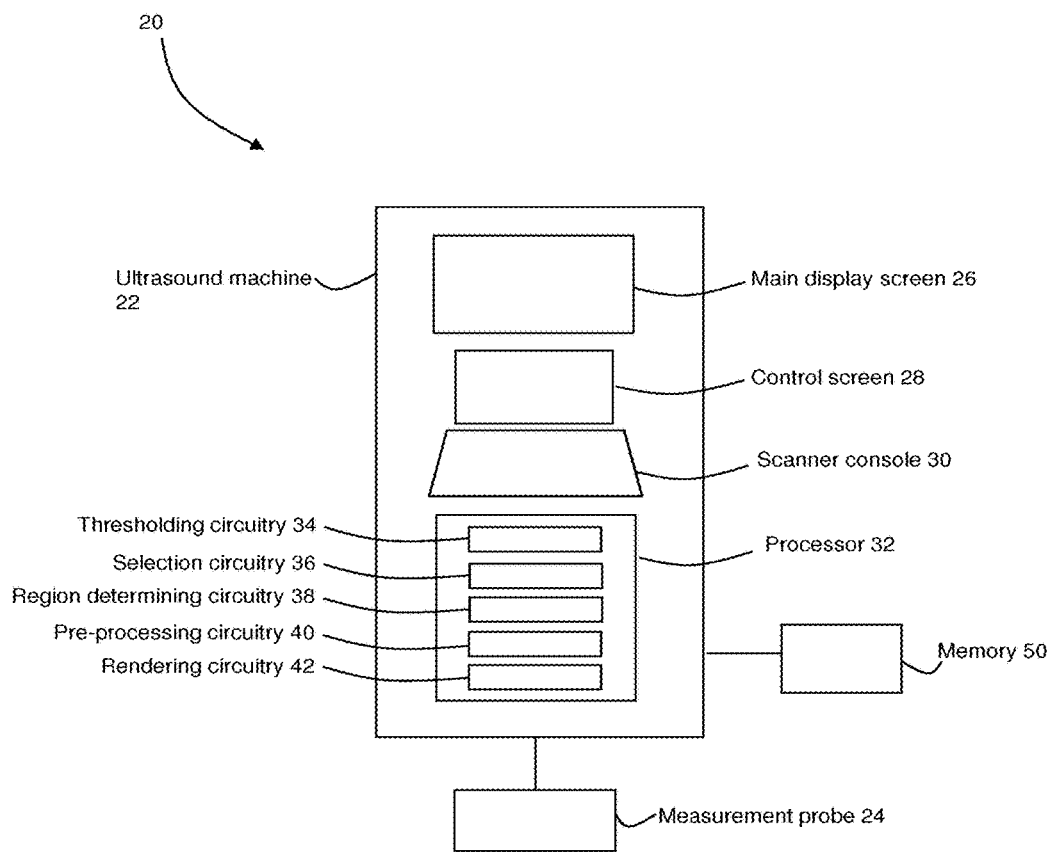
FIG. 2 is a schematic diagram of a diagnostic apparatus according to an embodiment.

An apparatus 20 according to an embodiment is illustrated schematically in FIG. 2. Apparatus 20 is configured to acquire data from a medical imaging scan and to process the acquired data to segment one or more desired tissue structures. In the present embodiment, the apparatus 20 processes images and/or image data and may be used as part of a diagnostic process. The apparatus 20 in this embodiment may be considered to be a medical diagnostic apparatus. The apparatus 20 in this embodiment may be considered to comprise a medical image processing apparatus.

In the present embodiment, apparatus 20 comprises an ultrasound machine 22 and associated probe 24. Any suitable type of ultrasound machine 22 and probe 24 may be used, for example any ultrasound machine 22 and probe 24 that are configured to obtain ultrasound image data that is suitable for 2D, 3D or 4D imaging. In other embodiments the apparatus 20 may comprise a scanner of an alternative modality, for example a CT scanner, cone-beam CT scanner, X-ray scanner, MR scanner, PET scanner or SPECT scanner.

The ultrasound machine 22 comprises a main display screen 26 for displaying a main ultrasound image, a control screen 28 for displaying control information, and a scanner console 30. In this embodiment, the scanner console 30 comprises an input device or devices such as input buttons or knobs, a computer keyboard, a mouse or a trackball. In alternative embodiments, the control screen 28 is a touch screen, which is both a display device and a user input device. Further embodiments may comprise a control screen 28, display screen or main display screen 26 that does not form part of the ultrasound machine 2. The ultrasound machine 22 also comprises a memory 50 for storing image data.

The ultrasound machine 22 comprises processing circuitry 32, for example a processor, for processing of data, including image data. The processing circuitry 32 comprises thresholding circuitry 34, selection circuitry 36 and region determining circuitry 38. In the present embodiment, the processing circuitry 32 comprises pre-processing circuitry 40 and rendering circuitry 42. In some embodiments, the processing circuitry 32 may also comprise diagnosis circuitry for performing a diagnosis.

Figure 3:
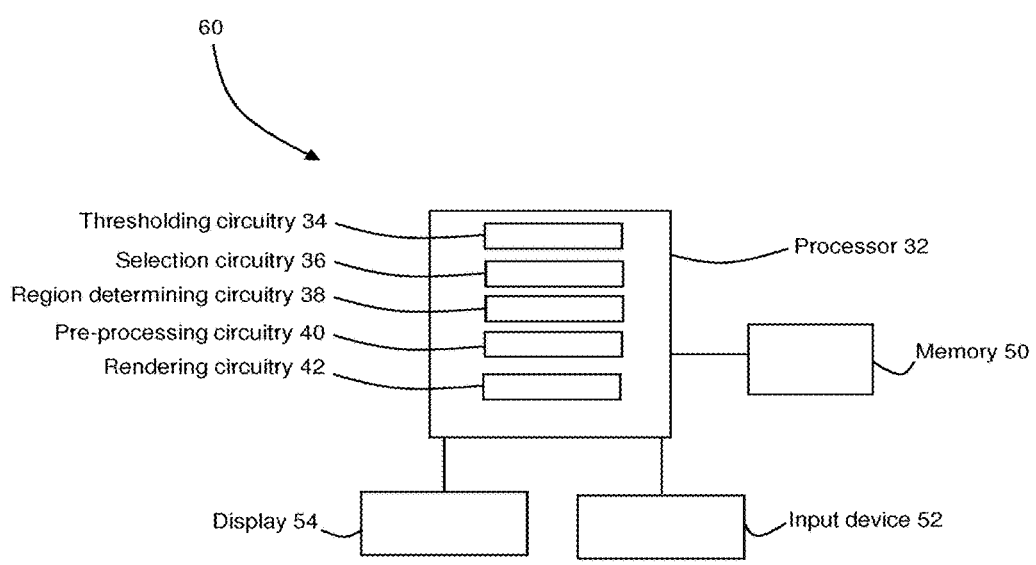
FIG. 3 is a schematic diagram of an image processing apparatus according to an embodiment.

An alternative embodiment is illustrated in the schematic diagram of FIG. 3. An apparatus 60 is configured to receive data that has previously been acquired by a separate scanner (such as an ultrasound machine, CT scanner, cone-beam CT scanner, X-ray scanner, MR scanner, PET scanner or SPECT scanner), and to process the received data to segment one or more tissue structures. The received data may comprise 2D, 3D or 4D medical image data.

Apparatus 60 comprises processing circuitry 32 comprising thresholding circuitry 34, selection circuitry 36 and region determining circuitry 38 and, in the present embodiment, pre-processing circuitry 40 and rendering circuitry. Apparatus 60 may comprise any suitable PC, workstation, terminal, tablet or other suitable computing apparatus. Apparatus 60 comprises at least one input device 52, for example a keyboard, mouse or touchscreen, and at least one display 54. Image processing apparatus 60 further comprises a memory 50. Apparatus 60 may be described as a medical image processing apparatus. In some embodiments, apparatus 60 may be a part of a medical diagnostic apparatus.

The processing circuitry 32 of FIG. 2 and FIG. 3 also includes a hard drive and other components including RAM, ROM, a data bus, an operating system including various device drivers, and hardware devices including a graphics card. Such components are not shown in FIG. 2 or 3 for clarity.

In each of the embodiments of FIG. 2 and FIG. 3, thresholding circuitry 34, selection circuitry 36 and region determining circuitry 38 are each implemented in processing circuitry 32 by means of a computer program having computer-readable instructions that are executable to perform the method of the embodiment. However, in other embodiments each of the thresholding circuitry 34, selection circuitry 36 and region determining circuitry 38 may be implemented in software, hardware or any suitable combination of hardware and software. In some embodiments, the various circuitries may be implemented as one or more ASICs (application specific integrated circuits) or FPGAs (field programmable gate arrays).

Figure 4:
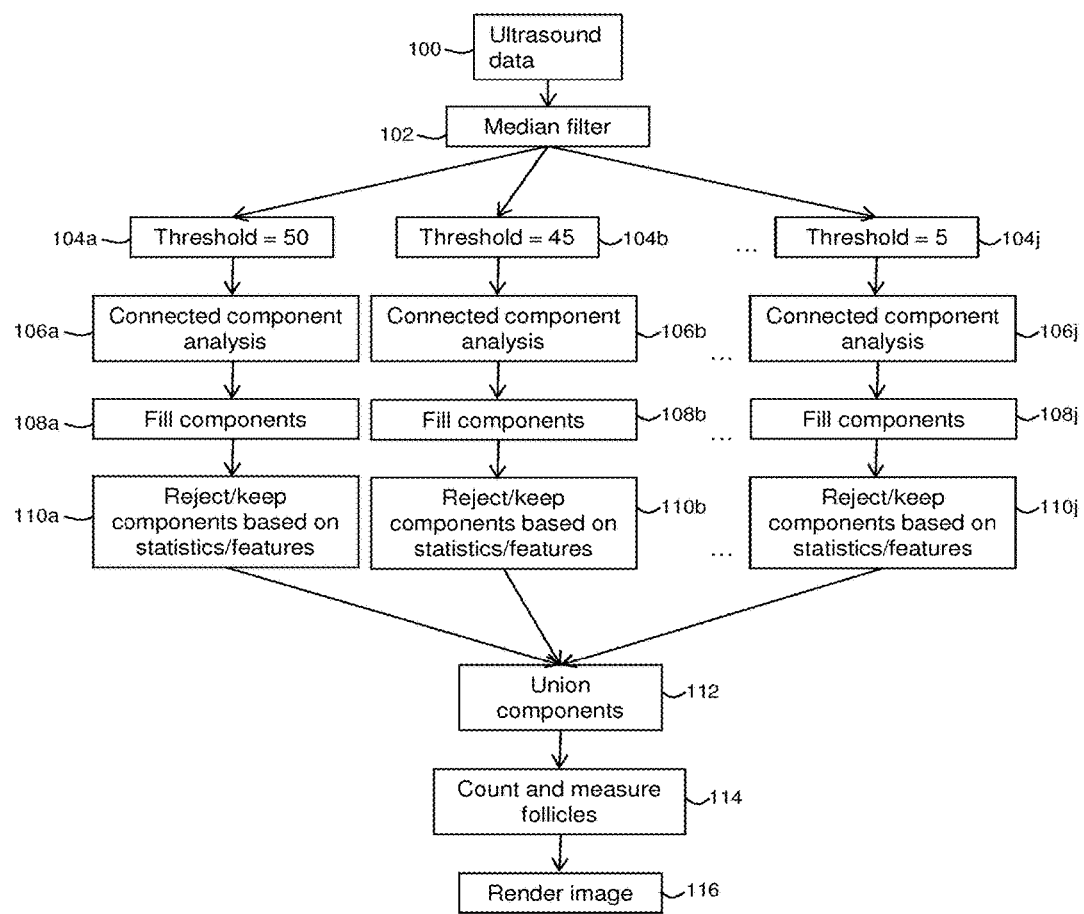
FIG. 4 is a flowchart illustrating in overview the process of an embodiment.

The system of FIG. 2 and the system of FIG. 3 are each configured to perform a process having a series of stages as illustrated in overview in the flow chart of FIG. 4.

At stage 100, the processing circuitry 32 operationally connects to the memory 50 and receives a set of medical image data from the memory 50. In the present embodiment, the medical image data comprises volumetric ultrasound data. In other embodiments, the data received may be 2D, 3D or 4D medical image data acquired using any suitable medical imaging modality.

The volumetric ultrasound data is representative of at least one tissue structure. In the present embodiment, the set of volumetric ultrasound data is representative of a plurality of follicles in an ovary. In other embodiments, the at least one tissue structure may comprise at least one follicle, cyst, kidney cyst, lung nodule, area of the lung affected by emphysema, gall stone, kidney stone, tumor, tumor nodule, hemorrhage or other appropriate tissue structure.

Figure 1:
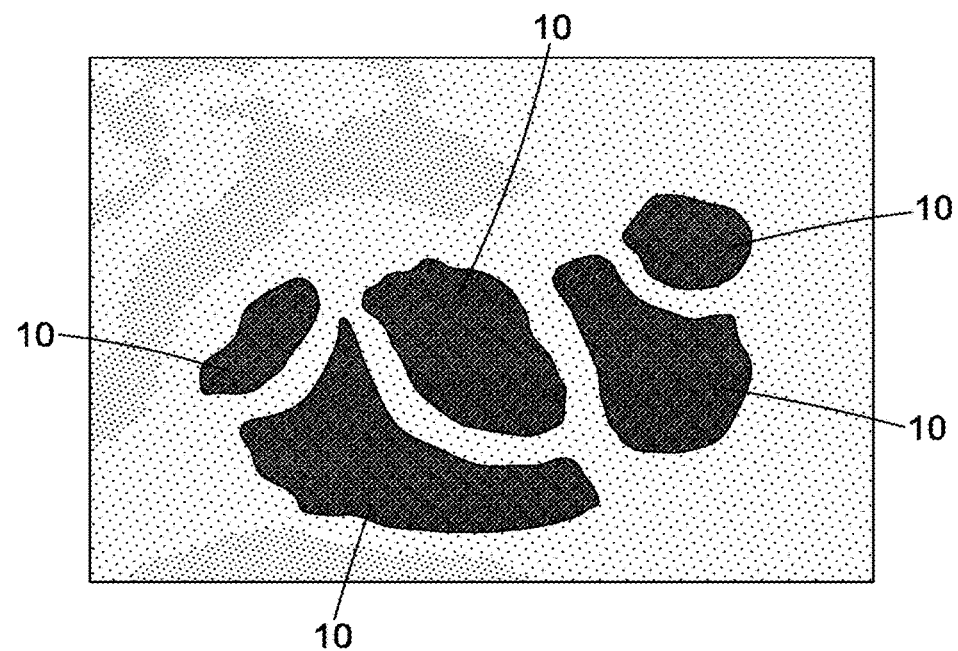
FIG. 1 is a schematic drawing that is representative of an ultrasound image showing a plurality of follicles.

FIG. 1 is a schematic drawing that is representative of an ultrasound image in which a plurality of follicles 10 are visible. The ultrasound image represents a slice taken through a volumetric ultrasound data set which has been obtained from an ultrasound scan of an ovary. Follicles 10 are hypo-echogenic in ultrasound. Therefore, in an ultrasound image, follicles 10 may look like dark chambers.

At stage 102, the pre-processing circuitry 40 applies a median filter to the medical image data set to obtain a pre-processed data set. The median filter has a smoothing effect and may reduce noise in the medical image data set. Ultrasound data is an example of a type of medical image data that is likely to be noisy. In alternative embodiments, the pre-processing circuitry may pre-process the medical image data set using any suitable pre-processing method, for example any pre-processing method that reduces noise in the medical image data set. The pre-processing may include shade correction. In some circumstances, the intensity of the image data may vary such that, for example, one side of the image data set is brighter than the other. Shade correction may reduce the extent of this shading across the field of view.

The pre-processing circuitry may pre-process the medical image data set using one or more filters. In the present embodiment, using a median filter to perform the pre-processing may provide a suitable compromise between quality and speed. In other embodiments, the pre-processing filter may be more complicated than a median filter. Any suitable filter or combination of filters may be used. The pre-processing circuitry 40 may pre-process the medical image data set using at least one of a median filter, a mean filter, a Gaussian filter, a Wiener filter, a bilateral filter, a variance filter, a bottom-hat filter or an anisotropic diffusion filter. In some circumstances, the anisotropic diffusion filter may be effective, but more computationally costly than some other filters.

In some embodiments, for example embodiments in which the received data is less likely to be noisy, the pre-processing of stage 102 may be omitted, or different pre-processing may be performed.

Figure 5A:
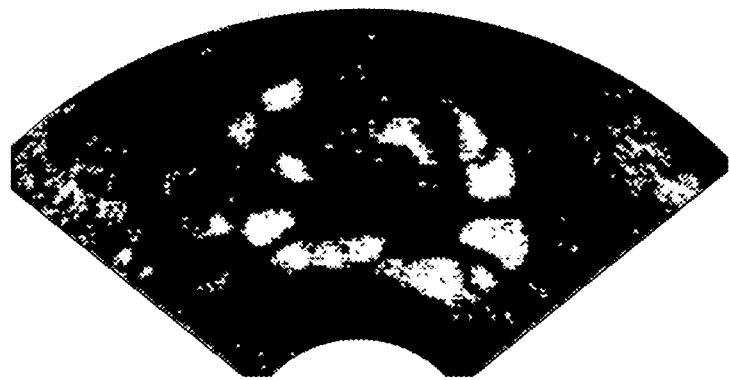
FIG. 5a is representative of a result of segmenting an image to which median filtering has not been applied.
Figure 5B:
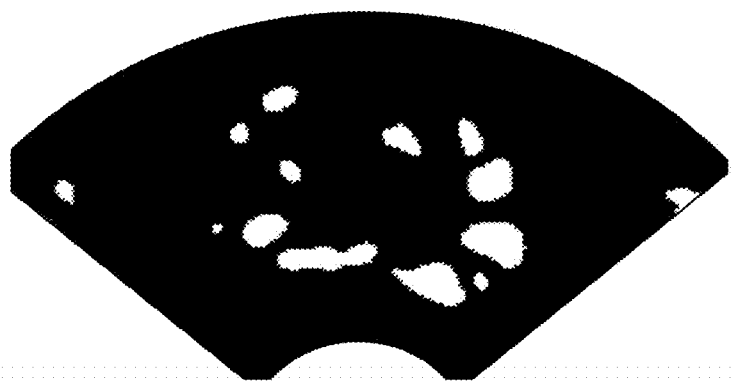
FIG. 5b is representative of a result of segmenting an image to which median filtering has been applied.

FIGS. 5a and 5b demonstrate an effect of median filtering on segmentation accuracy. Each of FIGS. 5a and 5b is representative of a slice through a volumetric ultrasound data set, which has been segmented using a single intensity threshold. FIGS. 5a and 5b represent the same slice, with and without median filtering. In FIGS. 5a and 5b, white pixels are representative of voxels having intensity below the intensity threshold (dark voxels, which may represent follicles) and black pixels are representative of voxels having intensity above the intensity threshold.

FIG. 5a shows a result of segmenting a set of ultrasound data to which no pre-processing filter has been applied. FIG. 5b shows a result of threshold-based segmentation of the same ultrasound data in which the segmentation is performed after a median filter has been applied to the ultrasound data. It may be seen that the results of thresholding are considerably noisier for an image to which no median filter has been applied (FIG. 5a) than for an image to which a median filter has been applied (FIG. 5b).

The pre-processing circuitry 40 passes the pre-processed data set to the thresholding circuitry 34. The pre-processed data set is a volumetric image data set comprising a plurality of voxels. Each voxel in the plurality of voxels has an associated intensity value, which is numerically lower for darker voxels and higher for lighter voxels. In other embodiments, the data set comprises a two-dimensional set of pixels and each pixel has an associated intensity value.

The thresholding circuitry 34 extracts regions from the pre-processed data set by performing threshold processing of the pre-processed data set using each of a plurality of threshold values. In the present embodiment, each threshold value is a voxel intensity value. The threshold values range from 5 to 50 in steps of 5. In other embodiments, different threshold values may be used. Each threshold value may be a threshold value for a different parameter or a threshold value for a combination of parameters. Where the medical image data set comprises two-dimensional data, the threshold value may be a pixel intensity value.

Each threshold value may be a threshold value for any suitable pixel- or voxel-related parameter. In some embodiments, each threshold value is a value for an image texture. Texture metrics may include any of a number of well-known quantitative texture metrics, for example greylevel co-occurrence matrices, run length greylevel matrices, Laws filters, wavelets, or fractals.

The threshold processing is performed using each threshold value individually. In the present embodiment, there are 10 different threshold values. Each of the 10 threshold values is applied to the pre-processed data set and a respective set of extracted regions is obtained for each of the 10 threshold values.

In the present embodiment, the threshold processing comprises stage 104 (applying each threshold to the pre-processed data set), stage 106 (performing connected component analysis on the components obtained by applying each threshold) and stage 108 (performing a morphological fill on the components that result from the connected component analysis). In other embodiments, stages 106 and/or 108 may be omitted. Stages 106 and 108 may comprise different operations, for example different morphological operations.

In FIG. 4, each of stages 104, 106 and 108 is shown as a plurality of sub-stages, one sub-stage for each threshold value. Stage 104 is divided into sub-stages 104a to 104j, although only three sub-stages are represented explicitly in the flow-chart of FIG. 4 for clarity. Stage 106 is divided into sub-stages 106a to 106j. Stage 108 is divided into sub-stages 108a to 108j.

We now consider the threshold processing that is performed for one threshold value, a threshold value of 50. The threshold value of 50 is used for sub-stages 104a, 106a and 108a which are each described in turn.

At sub-stage 104a, the thresholding circuitry 34 applies the threshold value of 50 to the pre-processed data set and divides the voxels of the pre-processed data set into a first category of voxels that have an intensity value below 50 and a second category of voxels that have an intensity value above 50.

The first category of voxels comprises voxels with low intensity values. Voxels that correspond to follicle tissue may have low intensity values. The first category of voxels may be considered to comprise candidate follicle voxels, which may be voxels that may be likely to belong to a follicle. The dividing of the voxels may be considered to be a segmentation.

At sub-stage 106a, the thresholding circuitry 34 performs connected component analysis on the candidate follicle voxels that were identified at sub-stage 104a, which are the voxels having an intensity value below the threshold value of 50. The connected component analysis results in a set of components. Each component is a group of connected voxels.

At sub-stage 108a, the thresholding circuitry 34 performs a morphological fill on the components identified in the connected component analysis of sub-stage 106a. The morphological fill may fill in any small holes in each component. The morphological fill should not enlarge any component. The thresholding circuitry 34 extracts a set of regions from the pre-processed data set. The extracted regions are the components that are present after the morphological fill of sub-stage 108a.

The threshold processing that was described above with reference to sub-stages 104a, 106a and 108a is also performed for each of the other threshold values. The threshold processing for the different threshold values may be performed simultaneously or sequentially. Considering sub-stage 104x to be representative of any of sub-stages 104b to 104j: at sub-stage 104x, the thresholding circuitry 34 applies the appropriate threshold value (for example, a threshold value of 45 for sub-stage 104b) to the pre-processed data set and divides the voxels of the pre-processed data set into a first category of voxels that have an intensity value below the threshold value and a second category of voxels that have an intensity value above the threshold value.

At sub-stage 106x, thresholding circuitry 34 performs connected component analysis on the candidate follicle voxels identified at stage 106x to obtain a set of components.

At sub-stage 108x, thresholding circuitry 34 performs a morphological fill on the components identified at stage 106x. The thresholding circuitry 34 extracts regions for the threshold value, which are the components resulting from the morphological fill of sub-stage 108x. The connected component analysis (and, in this case, the morphological fill) is applied to find sets of candidate follicles (extracted regions) at each threshold value, where the regions may be different for each threshold value.

Stages 104, 106 and 108 result in a set of extracted regions for each threshold value. Larger regions may be extracted using a high threshold (for example, 50) than are obtained using a low threshold (for example 5). More voxels are included in the first category of voxels (the category of voxels with intensities below the threshold value) when the threshold value is high than when the threshold value is low.

In the present embodiment, follicles present as dark regions in an image and so the voxels that are identified at stage 104 are voxels that are below the threshold value. In other embodiments, the tissue structure of interest may be a tissue structure that presents as a bright region in an image and the voxels that are identified at stage 104 may be voxels that are above the threshold value. The extracted regions may be regions of voxels having intensity above each threshold value.

Figure 6A:
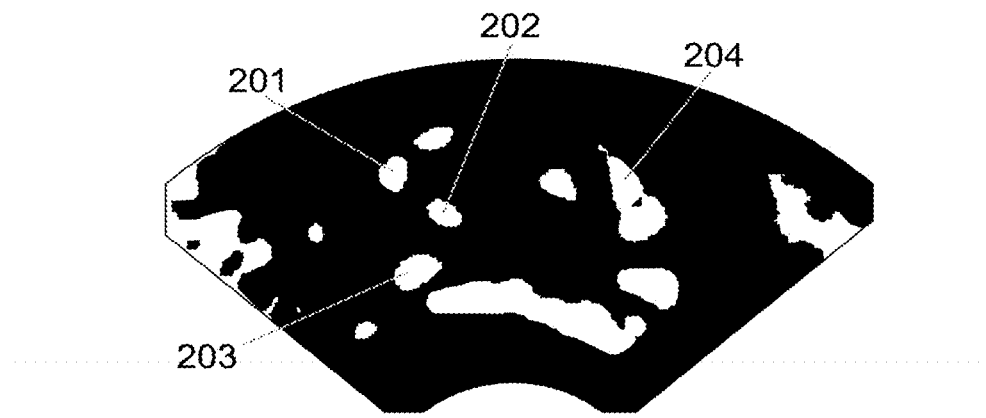
FIG. 6a is representative of an image segmented using a first threshold value.
Figure 6B:
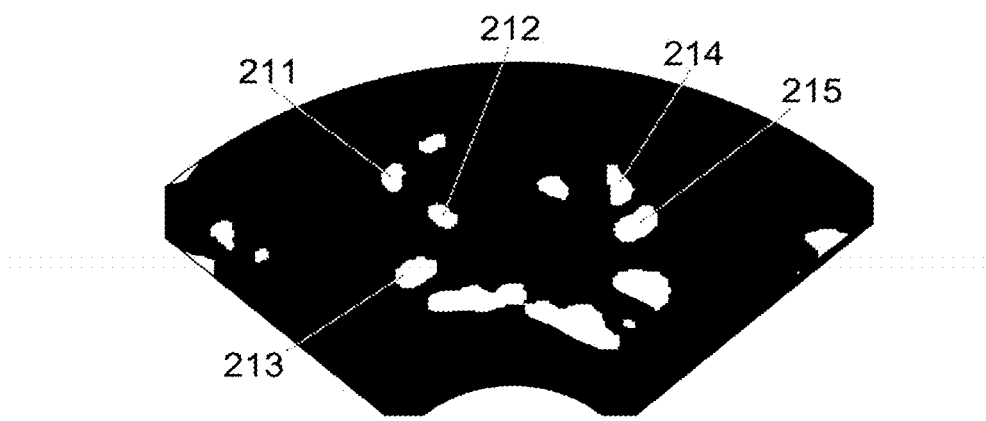
FIG. 6b is representative of an image segmented using a second threshold value.

FIGS. 6a and 6b are representative of results of applying different threshold values to the same slice of the same pre-processed data set. A threshold value of 45 has been applied to the pre-processed data set to obtain the results of FIG. 6a and a threshold value of 25 has been applied to the pre-processed data set to obtain the results of FIG. 6b. Connected component analysis and morphological clean up (for example, hole filling) have been performed on the voxels having an intensity value below the threshold value. Each connected group of voxels in FIGS. 6a and 6b is representative of an extracted region.

Only one slice is shown in FIGS. 6a and 6b. However, in the present embodiment, the threshold processing is applied to the full volumetric medical image data set, and therefore the extracted regions are three-dimensional regions. In other embodiments, threshold processing is applied to two-dimensional data and the extracted regions are two-dimensional regions.

It may be seen from FIGS. 6a and 6b that the image is differently segmented by thresholding using different threshold values. Different extracted regions are obtained by the different thresholds. Applying a threshold with a lower intensity value (for example, a threshold value of 25) results in smaller regions being extracted than applying a threshold with a higher intensity value (for example, a threshold value of 45). A region obtained by segmenting using a lower threshold value (for example, 25) may be a subset of the corresponding region that is obtained using a higher threshold value (for example, 45).

For example, regions 201, 202 and 203 of FIG. 6a correspond to regions 211, 212 and 213 respectively of FIG. 6b. A higher threshold is used in FIG. 6a, so more voxels are included in each region. Regions 201, 202 and 203 represent follicles that may be better segmented with a threshold of 45 than with a threshold of 25. A greater proportion of the size of each follicle is included in the regions of FIG. 6a than in the regions of FIG. 6b.

Region 204 of FIG. 6a has been identified as a single connected region. However, it may be seen that in FIG. 6b, two regions 214 and 215 correspond to region 204 of FIG. 6a. Using a threshold of 45 has caused the regions to be incorrectly merged. Regions 214 and 215 represent follicles that may be better segmented with a threshold of 25 than with a threshold of 45, since the threshold of 45 caused the follicles to be incorrectly merged.

For many sets of ultrasound image data or other medical imaging data, there may be no single threshold that is the best threshold for segmenting all the follicles in the image data. There can be a gradient of intensities across a single image. There may be shading within an image. Ultrasound may have a variety of artifacts, for example reverberations. Reverberation artifacts may artificially raise the intensity of an object.

Using a plurality of thresholds may allow each follicle to be segmented using a suitable threshold, even if the best threshold value for segmenting one follicle is different from the best threshold value for segmenting another follicle.

In the present embodiment, the thresholding circuitry 34 uses a predetermined set of threshold intensity values, which are intensity values from 5 to 50 in steps of 5. The filtered volume is thresholded at several predefined intensity levels. In other embodiments, the thresholding circuitry 34 may receive a set of threshold values from the memory 50, from another data store, or from user input. In some embodiments, the thresholding circuitry 34 may determine a set of threshold values, for example by determining the maximum and minimum intensity values for the pre-processed data set and dividing the resulting range of values by a given increment.

In the present embodiment, the threshold processing used to extract regions for each threshold value comprises applying a threshold, then applying connected component analysis and morphological fill to candidate follicle voxels that have been identified by using the threshold. In other embodiments, regions may be extracted based on the threshold in any suitable manner. Connected component analysis and morphological fill may or may not be used. Any suitable morphological operation may be performed on the voxels that are identified as candidate follicle voxels. A morphological operation may be performed before or after connected component analysis.

The output of stage 108 is a set of extracted regions for each threshold value. As described above, higher threshold values may result in larger extracted regions and/or more extracted regions than are obtained for lower threshold values. In some cases, there may be some threshold values for which no extracted regions are obtained.

The extracted regions are regions of dark voxels (voxels having intensity below each respective intensity threshold value). There may be several reasons for dark regions to be present in an ultrasound image. Some dark regions may be representative of follicles but others may be the result of, for example, image artifacts.

At stage 110, the selection circuitry 36 selects the extracted regions that meet at least one predetermined condition. The extracted regions that are selected may be extracted regions that are likely to represent follicles. Any suitable predetermined condition may be used in particular embodiments. The at least one predetermined condition may comprise criteria that may distinguish regions that are representative of follicles from regions that are not representative of follicles.

The at least one predetermined condition may be based on statistics or features of the extracted region. The extracted regions may be considered to be candidate follicles. Features of the extracted regions such as their diameter, volume and sphericity, are used to eliminate suspected false positives.

The at least one predetermined condition may comprise at least one size criterion, for example an area, a volume, a diameter, a minimum diameter or a maximum diameter. The at least one predetermined condition may comprise at least one shape criterion, for example circularity, sphericity or convex-hull ratio (the convex-hull ratio may be the ratio of the major to the minor axis of the convex hull of the extracted region). Any shape-related metric may be suitable. In some circumstances, the use of shape criteria may be difficult because follicles may be compressed, making them appear less spherical. The at least one predetermined condition may comprise asperity. The at least one predetermined condition may comprise a measure of intensity, for example a mean intensity or a variance of intensity for the extracted region.

The at least one predetermined condition may comprise at least one texture feature criterion. A variety of texture-like features can be calculated based on image values in a local neighborhood. Possible features may include (but are not limited to): gradient magnitude at multiple scales, gradient vector at multiple scales (for example, x, y, z gradient components), statistics from co-occurrence matrices, or features based on a wavelet transformation of the intensity in the neighborhood of the voxel, for example Haar texture features. Texture metrics may include any of a number of well-known quantitative texture metrics, for example greylevel co-occurrence matrices, run length greylevel matrices, Laws filters, wavelets, or fractals.

Stage 110 is shown in FIG. 4 as sub-stages 110a to 110j. In each of sub-stage 110a to 110j, a selection is made from the extracted regions that were obtained at the corresponding sub-stage 108a to 108j of stage 108.

In the present embodiment, the selection circuitry 38 classifies the extracted regions using a simple classifier, in this case a box classifier (also known as a linear classifier). If a given extracted region is classified by the classifier as a follicle, it is selected by the selection circuitry 36. If the extracted region is not classified as a follicle, it is not selected.

Different classifiers may be used in different embodiments. For example, a multivariate Gaussian, support vector machine, or other machine learning classifier may be used.

In the present embodiment, the classification is based on several predetermined conditions. The predetermined conditions comprise at least one size criterion, at least one shape criterion and at least one texture criterion. An extracted region will not be classified as a follicle if it does not meet a minimum size. An extracted region will not be classified as a follicle if it does not meet a sphericity criterion.

Figure 7A:
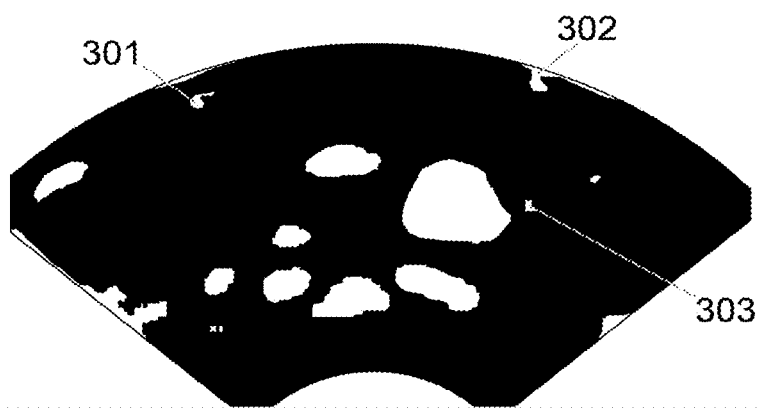
FIG. 7a is representative of a set of segmented regions.
Figure 7B:
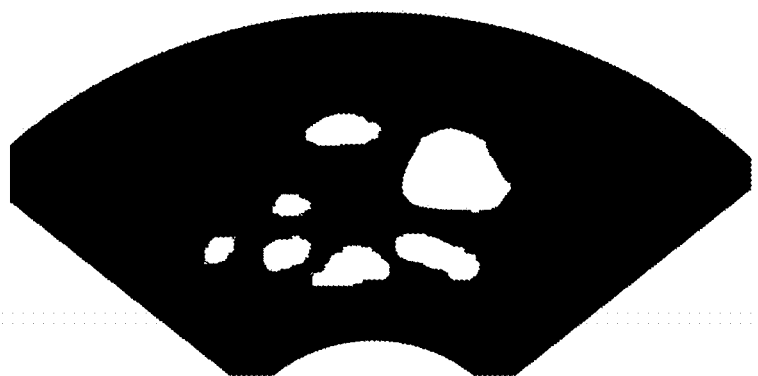
FIG. 7b is representative of selected regions from a set of segmented regions.

FIG. 7a shows a set of extracted regions (shown in white). Some of the extracted regions are representative of follicles, but some are not. FIG. 7b shows only the extracted regions that were selected from the extracted regions of FIG. 7a using a classifier. Extracted region 301 of FIG. 7a is correctly removed by the classifier because extracted region 301 does not meet a required shape constraint. Extracted region 302 of FIG. 7a is correctly removed by the classifier because the sphericity of extracted region 302 is too low. Extracted region 303 of FIG. 7a is correctly removed by the classifier because its radius is too small. Other components may be removed because they are connected to other large objects and so fail the size criterion.

The result of sub-stages 110a to 110j is a set of selected regions for each of the threshold values. It is possible that for some threshold values, no selected regions may be obtained. Different threshold values may result in different threshold regions. One follicle may be represented by several different selected regions obtained using different threshold values.

In the present embodiment, the same classifier using the same criteria is used on all of the extracted regions obtained using all of the threshold values. In other embodiments, different classifiers and/or different criteria may be used for extracted regions that were obtained using different threshold values.

Stage 112 uses all of the selected regions that were obtained using all the different threshold values. At stage 112, the region determining circuitry 38 performs a union of the selected regions to determine a set of final determined regions, each of which is considered to be representative of a follicle in the medical image data set. Any other suitable way of aggregating the selected regions may be used, as well as or instead of uniting the regions, in alternative embodiments.

Any given follicle may be represented by selected regions obtained with several different thresholds. The different selected regions obtained with the different thresholds may nest inside each other, since for any given follicle, a selected region for that follicle that was obtained with a lower threshold value should be a subset of a selected region for that follicle that was obtained with a higher threshold value.

The selected regions that correspond to a given follicle may be concentric or monotonic, and the use of a union or other aggregation may provide that regions that should not be merged are not merged together.

Extracted regions that are unlikely to be follicles have been ruled out in the selection of stage 110. Therefore, for a given follicle, the largest selected region representing that follicle may be the best representation of the follicle. The largest selected region will have been obtained with using a higher threshold than the other selected regions.

FIG. 8 shows a set of selected regions that were obtained for 5 different thresholds in images 401, 402, 403, 404 and 405. It may be seen that one selected region is obtained by using the threshold of image 401, and one different selected region is obtained by using the threshold of image 402. A different group of selected regions is obtained in each of images 403, 404 and 405. By taking a union of the selected regions (image 406) a set of regions is determined which includes more segmented follicles than any one of images 401 to 405. By using multiple thresholds on the same set of data and taking the union of the resulting selected regions, a greater number of follicles may be segmented than would be the case if only one threshold value was used. No single intensity threshold may be sufficient to accurately segment all the follicles, irrespective of size and position within the image.

In the present embodiment, the region determining circuitry 38 determines the regions that are representative of follicles by performing a union of the selected regions. However, the determination of regions that are representative of follicles is not limited to being performed based upon a union of the selected regions, and in alternative embodiments other processes are used to determine the regions that are representative of follicles.

For example, in some embodiments, the region determining circuitry 38 performs an intersection of the selected regions. For each follicle, determining an intersection may result in the smallest extracted region that represents that follicle. It is possible that performing an intersection may be used when counting but not measuring follicles.

In some further embodiments, for each follicle, the region determining circuitry 38 chooses one of the selected regions representing that follicle. For example, the region determining circuitry 38 may choose the region having the largest, smallest, or middle size from among the selected regions representing that follicle.

The region determining circuitry 38 may determine the region representing a follicle by selecting a typical region from among the selected regions for that follicle. In some embodiments, the selection circuitry 36 is configured to give a score with respect to each of the extracted regions and select the regions meeting the at least one predetermined condition based on the given scores at stage 110. The region determining circuitry 38 is configured to determine the region indicating the tissue structure by selecting the typical region based on the given scores. The typical region may be a region having typical values for any criterion. For a given follicle, typical values may be the values that are most representative of the selected regions representing that follicle (for example, a selected region having an average size or shape) or may be the values that are most follicle-like (for example, the highest sphericity).

In some embodiments, a set of criteria are applied to the regions resulting from the union. If there are multiple selected regions for the same follicle, the selection circuitry 36 uses at least one of the criteria to select one of the selected regions for that follicle. For example, the selection circuitry 36 may select the selected region that has the highest circularity. The criteria may be the same criteria as were applied at stage 110, or may be different criteria.

In other embodiments, each determined region resulting from the union is subjected to at least one fitness criterion. The determined region may be subjected to fitness criteria that are the same criteria as were applied at stage 110, or may be subjected to different fitness criteria. While the individual selected regions may pass the criteria, it is possible that the union of the selected regions for a given follicle may not pass the fitness criteria. If the addition of any one selected region makes the union of the selected regions fail the criteria, then that selected region may be removed from the union. In a scheme in which each subsequent threshold range includes the previous range, it should not normally be the case that individual selected regions pass the fitness criteria but the union of the individual selected regions fails to pass the fitness criteria (since the thresholded result from a given threshold range should be either equal to the result of the next threshold, or completely enclosed by the result of the next threshold). However, in some embodiments, different threshold ranges may be chosen where the next threshold did not completely include the result of the previous threshold, and where therefore the union may in some cases fail the fitness criteria.

In some embodiments, connected component analysis may be used again to label the union of the remaining regions (the determined regions), which may be returned to the user as the separate follicles. For example, connected component analysis may be used to give each follicle a unique label. In some embodiments, no connected component analysis is performed after the union of stage 112.

At stage 114, the region determining circuitry 38 counts and measures the regions that have been determined by the union of stage 112. These determined regions are considered to be representative of follicles. By counting the determined regions, the region determining circuitry 38 may obtain a count of the number of follicles that are represented in the medical image data set.

The region determining circuitry 38 may measure any suitable parameter of each determined region (for example area, volume, diameter, minimum diameter or maximum diameter) to obtain a measurement of the corresponding follicle. In the present embodiment, the region determining circuitry 38 measures the volume of each determined region and measures the maximum diameter of each determined region, to obtain measurements of the volume and maximum diameter of each follicle.

In other embodiments, any suitable measurement of each follicle may be performed. For example, a follicle may be measured along a particular axis or in a particular plane. A geometrical shape such as an ellipsoid (or ellipse) may be fitted to a determined region. The volume or area of the geometrical shape may be used to estimate the size of the follicle. In some embodiments, a position of each follicle may be determined.

The measurements obtained, for example the number and size of follicles, may be used to assess potential for harvesting eggs. In a further embodiment, apparatus 20 or 60 comprises diagnostic circuitry that is configured to obtain a diagnosis based on information that has been determined, for example based on the determined size and shape of each follicle or on the number of follicles.

At stage 116, the rendering circuitry 42 renders an image from the medical image data set and the determined regions. In the present embodiment, the rendering circuitry 42 renders an image of a slice of the medical image data set or pre-processed data set and overlays solid regions that are representative of the regions that were determined to be follicles. Each determined region may be represented in a different color. In other embodiments, each determined region may be outlined in the rendered image. Measurement information (for example, a list of follicle sizes) may be displayed with the rendered image. In some embodiments, no image is rendered and stage 116 is omitted. For example, in some embodiments, measurements of follicles may be obtained on stored data and may be provided to a user without a corresponding image being displayed. In some embodiments, measurements of follicles may be stored with the medical image data set from which they are obtained. In some embodiments, a rendered image and/or numerical values for a number and size of follicles may be stored to the patient's medical record.

By using the method of FIG. 4, measurement and counting of follicles may be automated. In some circumstances, automated measurement of follicles may be more repeatable and consistent than a manual measurement. Automatic 3D segmentation of follicles can be used to automate the counting and measurement of follicles, potentially saving time and reducing measurement error. Some measurements, for example particular diameters, may be more easily identified using automatic methods.

The use of multiple thresholds may be computationally efficient. It may not require much more run-time or computational power to apply multiple thresholds than to apply a single threshold. Some of the stages of the process of FIG. 4 are applied only to particular regions and therefore may be more efficient than if they were applied to the whole medical image data set or pre-processed data set. In some circumstances, the most computationally intensive stage of the process of FIG. 4 may be the pre-processing of stage 102 since it may be applied to the entire medical image data set.

By applying multiple thresholds, each follicle may be segmented at a good threshold value for that follicle, even when there is a gradient of intensity across an image such that the best threshold value for one follicle is different from the best threshold value for another follicle. The follicles may be small compared to the gradient across the image, such that the best threshold value does not change much across an individual follicle. Although the method above is described for ultrasound, it may also be applied to the segmentation of tissue structures in MR (and in other modalities). MR images may also have gradients in intensity across an image and therefore may have a different best threshold value for different tissue structures in an image.

Using a range of thresholds may accommodate the differences in intensity of different data sets. A single threshold value that is the best threshold value for one data set may not be the best threshold value for a different data set. However, it may be possible to determine a range of threshold values that is appropriate for use on many different data sets.

An object (i.e. the selected region of voxels corresponding to a follicle) that is identified using a higher threshold value may be a superset of the corresponding object identified using a lower threshold value. Therefore an object that is found at a lower threshold value (for example, 5) may also be found at a higher threshold value (for example, 10). However, it is possible that when the threshold value gets too high, too much tissue may be included. In such a case, the resulting extracted region may not meet the required predetermined conditions and so may not be selected. By taking a union, the largest selected region for a given follicle may be used as the determined region.

In the present embodiment, the process of FIG. 4 is not applied in real time. The process of FIG. 4 is applied in the post-processing of medical imaging data. For example, the process of FIG. 4 may be applied to stored ultrasound data as described above. However, in other embodiments, the process of FIG. 4 may be applied in real time during data acquisition.

In the embodiment described above with reference to FIG. 4, no user input is required. The medical image data set is automatically processed, follicles are automatically segmented, and the segmented follicles are automatically counted and measured.

In other embodiments, a user may provide input to the segmentation process. In some embodiments, some user input may be required. In some embodiments, user input may be optional.

In some embodiments, the user may supply a region of interest in which threshold processing is to be performed. For example, in some embodiments, an initial image is rendered from the medical image data set by the rendering circuitry 42 and displayed to the user, for example on main display screen 26. The user supplies a region of interest by selecting a region of the displayed initial image. For example, the region of interest may be defined by a two-dimensional or three-dimensional cuboid or lasso. Processing (for example, pre-processing and threshold processing) is only performed on the user-selected region of interest. Performing processing only on the user-selected region of interest may accelerate the process of FIG. 4. In other embodiments, the user may select a region of interest in the pre-processed data set. In further embodiments, the user may select a region of interest at any stage in processing, even once regions have been determined at stage 112.

In some embodiments, the rendering unit 42 renders an image in which the determined regions are displayed and identified as follicles. If the user believes that one of the determined regions has been incorrectly identified as a follicle, the user clicks on that determined region and that determined region is removed from the image and from the set of determined regions. The user may be allowed to delete incorrect follicles with a single click.

In some embodiments, the user may be allowed to add a follicle for which no region has been determined. For example, the user may be able to manually outline the follicle on an image rendered from the medical image data set or from the pre-processed data set. In some embodiments, the user input (for example, a manually outlined region) may be added as an extracted region or selected region in the process of FIG. 4. In some embodiments, the user input may be used as a starting point for a segmentation method.

In some embodiments, the user may be allowed to split a pair of follicles that have been incorrectly determined to be one region. For example, a user may click on the boundary between the two follicles and the region may be divided accordingly, or the user may outline two regions within the determined region, each representing a respective follicle. Any suitable user input may be used to divide the region into two regions.

In some embodiments, follicles are automatically measured and counted for many stored medical imaging data sets, for example in medical imaging data sets relating to different patients, or to different scans of the same patient. In some embodiments, no input from a user is required in order to measure and count the follicles. It may therefore become practical to measure and count the follicles in a large number of stored data sets.

Although methods are described above with reference to particular apparatuses 20 and 60, any suitable apparatus may be used. The method of any embodiment may be performed using any suitable apparatus or combination of apparatuses. For example, the method of FIG. 4 may be performed using a separate scanner and image processing apparatus. Features of any embodiment may be combined with features of any other embodiment.

The embodiments above are described with reference to the segmentation of follicles. However, in other embodiments, any other appropriate tissue structures may be segmented. For example, appropriate tissue structures may comprise cysts or other air or water pockets in other tissue, heart chambers, certain types of tumors or growths, or any other self-contained structures displaying a different overall brightness from the surrounding tissues. In some embodiments, the tissue structures may comprise hyperechoic tumors, for example liver, spleen, renal and other abdominal metastases. Tissue structures may be measured and counted. The measurement of tissue structures may comprise, for example, measuring a diameter, volume or position of a tissue structure.

Although the embodiments above are described with reference to processing of ultrasound data, in other embodiments data obtained using a different modality may be used, for example MR, CT, cone-beam CT, X-ray, PET or SPECT. Methods according to embodiments may be performed on 2D, 3D or 4D data.

Certain embodiments provide a method of segmenting and counting homogeneous objects in noisy images/volumes by:
1. Pre-processing to reduce noise
2. Applying multiple thresholds, and for each threshold
   a) Identifying connected components
   b) Rejecting components based on shape or intensity features
3. Forming the union of all accepted objects and re-applying connected component analysis.

The pre-processing may comprise or use a median filter, Gaussian filter, bi-lateral filter or anisotropic diffusion. The component rejection may be based on a combination of volume, sphericity, minimum and maximum diameter, mean intensity, variance intensity. The objects of interest may be ovarian follicles. The objects of interests may be cysts (for example, in the kidney).

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical image processing apparatus, comprising:
a memory to store medical image data representative of a tissue structure; and
processing circuitry configured to:
   operationally connect to the memory;
   for each of a plurality of threshold values, extract a respective set of regions from the medical image data by performing threshold processing of the medical image data using the threshold values, wherein the same medical image data is processed using each of the threshold values;
   select regions meeting at least one predetermined condition from among the respective sets of extracted regions; and
   determine a region representative of the tissue structure in the medical image data by combining the selected regions corresponding to the tissue structure,
   wherein the selected regions are candidate regions that may represent the tissue structure obtained using the plurality of threshold values;
   the determining of the region representative of the tissue structure comprises determining a plurality of regions representative of a plurality of the tissue structures, and
   at least some of the plurality of regions are determined by the processing circuitry by aggregating candidate regions obtained at different ones of the threshold values.

2. The medical image processing apparatus according to claim 1, wherein the aggregating comprises performing a union or intersection process.

3. The medical image processing apparatus according to claim 1, wherein the tissue structure comprises at least one of a follicle, a cyst, a kidney cyst, a lung nodule, an area of a lung affected by emphysema, a gall stone, a kidney stone, a tumor, a tumor nodule, a hemorrhage.

4. The medical image processing apparatus according to claim 1, wherein each of the plurality of threshold values depend on pixel or voxel values indicating the tissue structure in the medical image.

5. The medical image processing apparatus according to claim 1, wherein each of the plurality of threshold values comprises an intensity value.

6. The medical image processing apparatus according to claim 1, wherein the threshold processing of the medical image data comprises, for each threshold value of the plurality of threshold values, selecting voxels or pixels based on the threshold value, and using connected component analysis to group the voxels or pixels into regions.

7. The medical image processing apparatus according to claim 6, wherein the threshold processing of the medical image data further comprises performing at least one morphological operation on the voxels, pixels or regions.

8. The medical image processing apparatus according to claim 1, wherein the at least one predetermined condition comprises a predetermined condition concerning a value or other property of at least one of: area, volume, circularity, sphericity, diameter, minimum diameter, maximum diameter, asperity, convex-hull ratio, intensity, mean intensity, variance intensity, a texture feature.

9. The medical image processing apparatus according to claim 1, wherein the processing circuitry is further configured to measure the determined region that is representative of the tissue structure in the medical image data, thereby to obtain a measurement of the tissue structure.

10. The medical image processing apparatus according to claim 1, wherein the medical image data is representative of the plurality of the tissue structures, and wherein the processing circuitry is further configured to determine the plurality of regions, each representative of a respective tissue structure.

11. The medical image processing apparatus according to claim 8, wherein the processing circuitry is further configured to count the determined regions, thereby to count the tissue structures.

12. The medical image processing apparatus according to claim 1, wherein the processing circuitry is further configured to filter the medical image data before extracting regions from the medical image data.

13. The medical image processing apparatus according to claim 1, wherein the medical image data comprises image data generated by at least one of: an ultrasound diagnosis apparatus, an X-ray diagnosis apparatus, an X-ray CT apparatus, an MRI apparatus.

14. The medical image processing apparatus according to claim 1, wherein the medical image processing apparatus is a part of a medical diagnosis apparatus.

15. The medical image processing apparatus according to claim 14, wherein the medical diagnosis apparatus comprises at least one of: an ultrasound diagnosis apparatus, an X-ray diagnosis apparatus, an X-ray CT apparatus, an MRI apparatus.

16. A medical image processing method, comprising:
operationally connecting to a memory, in which is stored medical image data representative of a tissue structure;
for each of a plurality of threshold values, extracting a respective set of regions from the medical image data by performing threshold processing of the medical image data using the threshold values, wherein the same medical image data is processed using each of the threshold values;
selecting regions meeting at least one predetermined condition from among the respective sets of extracted regions; and
determining a region representative of the tissue structure in the medical image data by combining the selected regions corresponding to the tissue structure,
wherein the selected regions are candidate regions that may represent the tissue structure obtained using the plurality of threshold values;
the step of determining the region representative of the tissue structure comprises determining a plurality of regions representative of a plurality of the tissue structures, and
at least some of the plurality of regions are determined by aggregating candidate regions obtained at different ones of the threshold values.

17. A non-transitory computer-readable storage medium storing a computer program comprising computer-readable instructions that are executable to perform a method comprising:
operationally connecting to a memory, in which is stored medical image data representative of a tissue structure;
for each of a plurality of threshold values, extracting a respective set of regions from the medical image data by performing threshold processing of the medical image data using the threshold values, wherein the same medical image data is processed using each of the threshold values;
selecting regions meeting at least one predetermined condition from among the respective sets of extracted regions; and
determining a region representative of the tissue structure in the medical image data by combining the selected regions corresponding to the tissue structure,
wherein the selected regions are candidate regions that may represent the tissue structure obtained using the plurality of threshold values;
the step of determining the region representative of the tissue structure comprises determining a plurality of regions representative of a plurality of the tissue structures, and
at least some of the plurality of regions are determined by aggregating candidate regions obtained at different ones of the threshold values.

18. A medical image processing apparatus, comprising:
a memory configured to store medical image data representative of a tissue structure; and
processing circuitry configured to
operationally connect to the memory;
for each of a plurality of threshold values, extract a respective set of regions from the medical image data by performing threshold processing of the medical image data using the threshold values, wherein the same medical image data is processed using each of the threshold values;
give a score with respect to each of the extracted regions;
select regions meeting at least one predetermined condition from among the respective sets of extracted regions, based on the given scores; and
determine a region indicating the tissue structure by selecting, from among the selected regions corresponding to the tissue structure, typical regions to be combined based on the given scores.

19. A medical image processing method, comprising:
storing medical image data representative of a tissue structure;

operationally connecting to a memory;

for each of a plurality of threshold values, extracting a respective set of regions from the medical image data by performing threshold processing of the medical image data using the threshold values, wherein the same medical image data is processed using each of the threshold values;

giving a score with respect to each of the extracted regions;

selecting regions meeting at least one predetermined condition from among the respective sets of extracted regions, based on the given scores; and determining a region indicating the tissue structure by selecting, from among the selected regions corresponding to the tissue structure, typical regions to be combined based on the given scores.

20. A non-transitory computer-readable storage medium storing a computer program comprising computer-readable instructions that are executable to perform a method comprising:

storing medical image data representative of a tissue structure;

operationally connecting to a memory;

for each of a plurality of threshold values, extracting a respective set of regions from the medical image data by performing threshold processing of the medical image data using the threshold values, wherein the same medical image data is processed using each of the threshold values;

giving a score with respect to each of the extracted regions;

selecting regions meeting at least one predetermined condition from among the respective sets of extracted regions, based on the given scores; and determining a region indicating the tissue structure by selecting, from among the selected regions corresponding to the tissue structure, typical regions to be combined based on the given scores.

* * * * *